United States Patent [19]

Rosenberg

[11] Patent Number: 4,713,000
[45] Date of Patent: Dec. 15, 1987

[54] MOLAR CONTROLLING AND POSITIONING ORTHODONTIC APPLIANCE ADJUSTABLE IN THREE PLANES

[76] Inventor: Farel Rosenberg, 10535 Wilshire Blvd., Los Angeles, Calif. 90024

[21] Appl. No.: 14,631

[22] Filed: Feb. 12, 1987

[51] Int. Cl.⁴ ............................................... A61C 7/00
[52] U.S. Cl. ......................................... 433/18; 433/7; 433/19
[58] Field of Search ........................ 433/17, 7, 18, 5, 6

[56] References Cited

U.S. PATENT DOCUMENTS

| | | | |
|---|---|---|---|
| 3,477,129 | 11/1967 | Rubin | 433/17 |
| 3,835,540 | 9/1974 | Biederman | 433/7 |
| 4,571,178 | 2/1986 | Rosenberg | 433/7 |

Primary Examiner—Robert Peshock
Attorney, Agent, or Firm—Gilbert Kivenson

[57] ABSTRACT

An orthodontic appliance for moving molars in a backward direction or achieving controlled slippage in a forward direction is described. The appliance provides improved installation, adjustment and retention features which are based on in-place crimping techniques.

1 Claim, 3 Drawing Figures

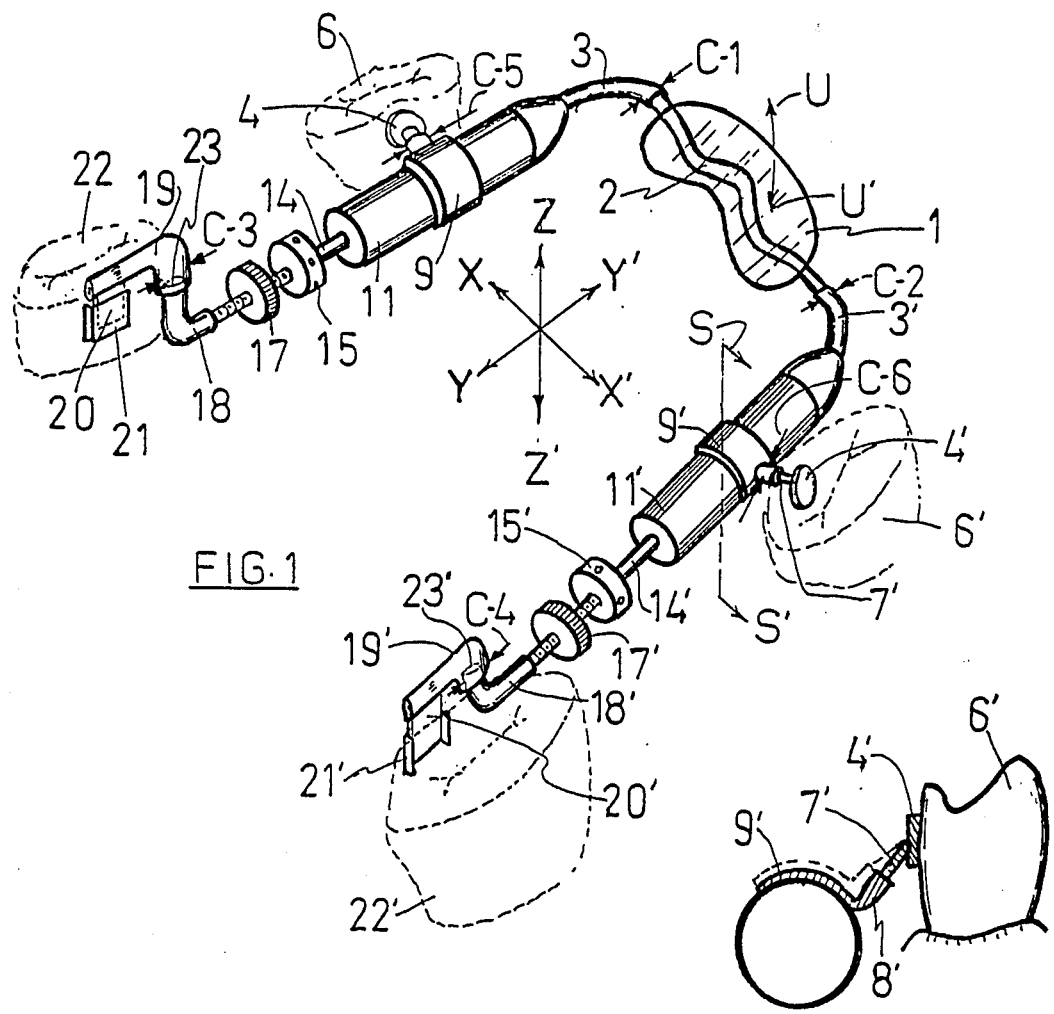
FIG. 1
FIG. 2
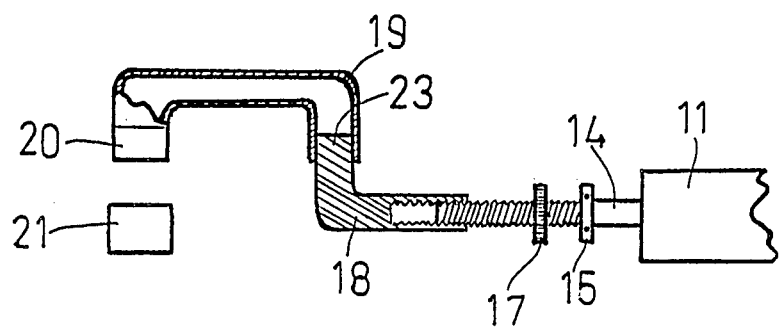
FIG. 3

MOLAR CONTROLLING AND POSITIONING ORTHODONTIC APPLIANCE ADJUSTABLE IN THREE PLANES

BACKGROUND OF THE INVENTION

This invention relates to improvements in my Forward-Backward Molar Controlling and Positioning Dental Appliance, U.S. Pat. No, 4,571,178. Although my earlier invention is useable for its intended purposes such as the movement of molars in a backward direction or controlled slippage in the forward direction to achieve various orthodontic objectives, it has been found that a means for vertical adjustment was required for proper fitting of the appliance. In addition, stabilization of the appliance was found to be more effective when carried out by extending wires from certain teeth to the appliance rather than the reverse. It was also found that the assembly of the appliance for a given case was more effective and a custom fit could be better obtained if done in the mouth rather than externally and then the molar controlling and positioning function brought about by the spring-driven screw advance mechanism.

It is an objective of the present, improved invention to provide a simple means of installing, assembling, adjusting and stabilizing in three dimensions the previously described appliance while losing none of its advantages. In-place assembly is carried out in the present improvement by crimping, a procedure which insures dimensional stability.

DESCRIPTION OF THE DRAWINGS

The operation of the invention will be described with reference to FIGS. 1, 2 and 3.

FIG. 1 is an isometric view of the invention as it would be installed in the lower part of the mouth. A similar unit without provision for the frenum would be installed in the upper part of the mouth.

FIG. 2 is a right side view of the stabilizing means along the line S—S' of FIG. 1.

FIG. 3 is a left side view of the screw advance mechanism and the molar anchoring means.

DESCRIPTION OF THE INVENTION

The present appliance like its predessor is anchored between tissue covered basal bone and the rear teeth and is held in place by stabilization extensions from lingual buttons cemented to forward teeth. The forward anchoring is brought about by a semirigid pad 1 molded around a wire 2. Undulations in the wire prevent pad 1 from working loose and being free to turn in the direction U-U' (FIG. 1). During installation the appliance's width (X-X') is adjusted by sliding the ends of wire 2 into the tubing 3 and 3' so that a proper fit is obtained in the patient's mouth. The tubing is then crimped at points C-1 and C-2.

Piston rods 14 and 14' extend from internal spring loaded pistons in the chambers 11 and 11' and are threaded over a portion of their lengths as in my previous invention. The threaded ends mate with the internally threaded connecting fixtures 18 and 18' which are bent through 90 degrees; the ends 23 and 23' are slidably contained in the tubes 19 and 19' respectively (FIGS. 1 and 3). The ends of the tubes 19 and 19', which are parts of the molar attachment, are flattened at 20 and 20' to fit into the molar receptacles 21 and 21' which have previously been cemented or otherwise attached to the lingual surfaces of the molars chosen to be moved or stabilized. Vertical adjustment in the direction Z—Z' is made by sliding ends 23 and 23' in and out of the tubes 19 and 19' to fit the appliance to the patient's mouth. The adjustment is then locked in by crimping at C-3 and C-4.

Buttons 4 and 4' are cemented to forward teeth 6 and 6'. (FIG. 2). Wires 7 and 7', rigidly attached to the buttons, fit slidably into tubes 8 and 8' which are part of the retaining plates 9 and 9'. The latter rest on the chambers 11 and 11'. When adjusted, the retaining plates 9 and 9' prevent the appliance from working loose in the mouth. When this adjustment is made, it is locked in by crimping at C-5 and C-6. Wires 7 and 7' may be made sufficiently flexible to permit plates 9 and 9' to be moved by the orthodontist to allow the appliance to be removed and then reinstalled in the mouth.

After installation and adjustment the appliance is utilized in applying orthodontic forces as required in the posterior direction Y and controlling counter-slippage forces in the direction Y'. This is done by turning of the adjustment disks 15 and 15' and locking the threaded portion of the rods 14 and 14' with the lock nuts 17 and 17' as in my previous invention.

I claim:

1. A dental appliance for use as a tooth movement inhibitor, inducer and controller comprised in combination of:
   a. a plate shaped to bear against tissue-covered basal bone areas, said plate being mounted about and partially enclosing a primary rod;
   b. cylindrical force exerting members on both sides of the appliance each of the members terminating at one end in tubing to slidably and crimpably fit over an end of the primary rod for horizontal adjustment and fitting of the appliance;
   c. springs contained within said cylindrical force exerting members;
   d. piston heads contained within said cylindrical force exerting members and pressing against the springs and terminating in threaded piston rods;
   e. connecting fixtures which are internally threaded to receive the threaded piston rods on their forward ends, said fixtures terminating in vertical extensions;
   f. u-shaped tubing sections which slide over and are crimpable to said vertical extension of the connecting fixtures on each side of the appliance and are flattened at their far ends to fit into receptacles which have been previously cemented to rear molars;
   g. retaining plates which bear on the surfaces of the cylindrical force exerting members, said retaining plates having hollow neck sections which slide over and are crimpably mounted to wires extending from buttons attached to the lingual surface of forward teeth on each side of the mouth;

whereby the appliance is assembled in the mouth, the crimpable fits between said primary rod and the force exerting members, between the tubing sections mounting in the molar receptacles and the connecting fixtures, and between the retainplates, hollow necks and the wires extending from the buttons cemented to the lingual surfaces of the forward teeth are adjusted as the individual case need dictate and then crimped to hold the appliance rigidly in the mouth to permit subsequent rotation of the threaded pistons in carrying out backward tooth movement, movement inhibition or controlled forward slippage.

* * * * *